(12) United States Patent
Oya et al.

(10) Patent No.: US 9,255,077 B2
(45) Date of Patent: *Feb. 9, 2016

(54) FLUORINE ATOM-CONTAINING MERCAPTO COMPOUND

(71) Applicant: FUJIFILM CORPORATION, Tokyo (JP)

(72) Inventors: Toyohisa Oya, Kanagawa (JP); Tokihiko Matsumura, Kanagawa (JP); Yasuaki Matsushita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/729,931

(22) Filed: Jun. 3, 2015

(65) Prior Publication Data

US 2015/0266840 A1 Sep. 24, 2015

Related U.S. Application Data

(63) Continuation of application No. PCT/JP2013/083092, filed on Dec. 10, 2013.

(30) Foreign Application Priority Data

Dec. 13, 2012 (JP) .................................. 2012-272418

(51) Int. Cl.
*C07D 285/125* (2006.01)
(52) U.S. Cl.
CPC .................................. *C07D 285/125* (2013.01)
(58) Field of Classification Search
CPC .................................................. C07D 285/125
See application file for complete search history.

(56) References Cited

FOREIGN PATENT DOCUMENTS

| JP | 2001-019686 A | 1/2001 |
|---|---|---|
| JP | 2001019686 A * | 1/2001 |

OTHER PUBLICATIONS

T.H. James, The Theory of the Photographic Process, p. 397.
Notification of Transmittal of Translation of the International Preliminary Report on Patentability (Chapter I) and Translation of Written Opinion of the International Searching Authority; PCT/JP2013/083092; issued on Jun. 25, 2015.

* cited by examiner

*Primary Examiner* — Matthew Coughlin
(74) *Attorney, Agent, or Firm* — Studebaker & Brackett PC

(57) ABSTRACT

A mercapto compound is represented by formula (1)

[Chemical Formula 1]

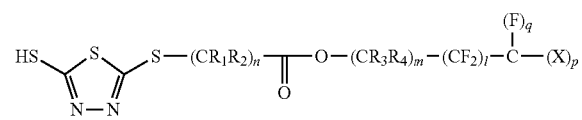

Formula (1)

(in formula (1), $R_1$ and $R_2$ each independently represent a hydrogen atom or an alkyl group; $R_3$ and $R_4$ each independently represent a hydrogen atom or a substituent; n represents 1 or 2; m represents an integer of 1 to 6; l represents an integer of 1 to 6; q represents 0 or 1; p represents 2 or 3; p+q represents 3; X represents a perfluoroalkyl group having 1 to 14 carbon atoms; when n is 2, structures of units represented by $CR_1R_2$ may be identical to or different from each other; and when m is 2 or more, structures of units represented by $CR_3R_4$ may be identical to or different from each other). The mercapto compound is novel and has excellent affinity for a fluorine-containing polymer and a fluorine-containing solvent.

1 Claim, No Drawings

FLUORINE ATOM-CONTAINING MERCAPTO COMPOUND

CROSS-REFERENCE TO RELATED APPLICATIONS

This application is a Continuation of PCT International Application No. PCT/JP2013/083092 filed on Dec. 10, 2013, which claims priority under 35 U.S.C. §119(a) to Japanese Patent Application No. 2012-272418 filed on Dec. 13, 2012. Each of the above application(s) is hereby expressly incorporated by reference, in its entirety, into the present application.

BACKGROUND OF THE INVENTION

The present invention relates to a fluorine atom-containing mercapto compound and more specifically relates to a fluorine atom-containing mercapto compound having excellent compatibility with a fluorine-containing polymer and a fluorine-containing solvent.

Mercapto compounds (mercapto group-containing compounds) are widely used in industrial applications such as chain transfer agents in radical polymerization reactions, rubber vulcanization accelerators, photographic additives, anticorrosives, synthesis intermediates of pharmaceutical products and industrial chemicals, metal surface modifiers, physiologically active substances, curing agents, crosslinking agents and plastic modifiers. In particular, a mercapto compound containing a nitrogen-containing heterocyclic ring has the property of easily forming a chemical bond with or easily adsorbing metals such as gold, silver and copper in an elemental or ionic form, and hence is particularly useful as an additive for silver halide photographic sensitive materials (e.g., this compound is widely used as an antifogging agent or a stabilizer by being added to a silver halide photographic sensitive material or a photographic treatment liquid) (T. H. James, The theory of the photographic process, page 397), an anticorrosive, a metal surface modifier and the like.

In recent years, fluorochemical materials (fluorine atom-containing materials) having functions such as durability improvement, surface modification and corrosion protection are industrially widely used. The fluorochemical materials allow, for example, polymer materials to achieve higher functionality (durability improvement and surface modification of polymers or protection of contacting metal against corrosion), and metal or non-metal materials to achieve higher functionality (durability improvement, surface modification or corrosion protection by means of addition or coating) (JP 2001-19686 A).

SUMMARY OF THE INVENTION

However, mercapto compounds (mercapto group-containing compounds) bleed out from the materials because of their low affinity for fluorine-containing polymers (fluororesins) and fluorine-containing solvents, and hinder production of coating liquids because of their low solubility, and it has been sought to improve such problems.

In view of the situation as described above, an object of the present invention is to provide a novel mercapto compound having excellent affinity for a fluorine-containing polymer and a fluorine-containing solvent.

Under these circumstances, the inventors of the present invention have made an intensive study and as a result found a novel mercapto compound having a specific fluorine-containing alkyl group in the molecule and thus completed the present invention.

More specifically, the foregoing object is achieved by the following means.

(1) A compound represented by formula (1) to be described later.

The present invention can provide a novel mercapto compound having excellent affinity for a fluorine-containing polymer and a fluorine-containing solvent.

Compounds represented by formula (1) to be described later include a specific fluorine-containing alkyl group in the molecule, and hence are particularly useful as chain transfer agents in radical polymerization reactions, rubber vulcanization accelerators, photographic additives, anticorrosives, synthesis intermediates of pharmaceutical products and industrial chemicals, metal surface modifiers, physiologically active substances, curing agents, crosslinking agents and the like.

DETAILED DESCRIPTION OF THE INVENTION

Preferred embodiments of a fluorine atom-containing mercapto compound according to the invention are described below.

The characteristic features of the invention compared to the prior art are first described in detail.

Reasons why a mercapto azole compound having a specific fluorine-containing alkyl group in the molecule according to the invention improves the affinity for fluorine-containing polymers and fluorine-containing solvents are not clarified in detail but the following mechanism is estimated. More specifically, the present invention is characterized by inclusion of a fluorine-containing alkyl group in an azole (thiadiazole) ring via a linking group. On the other hand, the azole ring is substituted with an SH group having high polarizability. Having the characteristics as described above, this compound is more likely to form, in a fluorine-containing polymer or a fluorine-containing solvent, a micelle-like structure having a fluorine-containing alkyl group located on the surface side and the compound of the invention is particularly deemed to have an unexpected effect that the affinity for fluorine-containing polymers and fluorine-containing solvents is improved because the surface fluorine atom density is more increased by the branched structure of the terminal of the fluorinated alkyl group.

(Compound Represented by Formula (1))

A compound (fluorine atom-containing mercapto compound) represented by formula (1) is described below in detail.

[Chemical Formula 1]

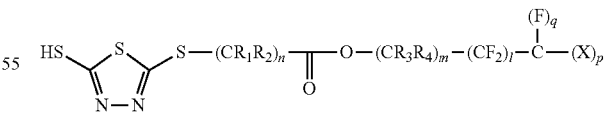

Formula (1)

In formula (1), $R_1$ and $R_2$ each independently represent a hydrogen atom or an alkyl group. n represents 1 or 2 and preferably 2. When n is 2, structures of units represented by $CR_1R_2$ may be identical to or different from each other. The alkyl group may have a substituent.

When $R_1$ and $R_2$ each represent an alkyl group, the alkyl group preferably contains 1 to 30 carbon atoms, more preferably 1 to 15 carbon atoms and most preferably 1 to 6 carbon atoms, preferable examples thereof including methyl, ethyl, n-propyl, isopropyl, t-butyl, n-octyl, eicosyl, chloromethyl, hydroxymethyl, aminoethyl, N,N-dimethylaminomethyl, 2-chloroethyl, 2-cyanoethyl, 2-hydroxyethyl, 2-(N,N-dimethylamino)ethyl, and 2-ethylhexyl.

The structure represented by $(CR_1R_2)_n$ is preferably —$CH_2$—, —$CH_2CH_2$—, or —$CH_2CH(CH_3)$—, more preferably —$CH_2CH_2$—, or —$CH_2CH(CH_3)$—, and most preferably —$CH_2CH_2$—.

$R_3$ and $R_4$ each independently represent a hydrogen atom or a substituent. m represents an integer of 1 to 6. When m is 2 or more, structures of units represented by $CR_3R_4$ may be identical to or different from each other. $R_3$ and $R_4$ may also be bonded together to form a ring.

The substituents represented by $R_3$ and $R_4$ represent, for example, any of the following: halogen atoms (e.g., chlorine atom, bromine atom and iodine atom); alkyl groups [representing optionally substituted, linear, branched or cyclic alkyl groups including alkyl groups (preferably alkyl groups having 1 to 30 carbon atoms, such as methyl, ethyl, n-propyl, isopropyl, t-butyl, n-octyl, eicosyl, 2-chloroethyl, 2-cyanoethyl, and 2-ethylhexyl), cycloalkyl groups (preferably optionally substituted cycloalkyl groups having 3 to 30 carbon atoms, such as cyclohexyl, cyclopentyl, and 4-n-dodecylcyclohexyl), and bicycloalkyl groups (preferably optionally substituted bicycloalkyl groups having 5 to 30 carbon atoms, i.e., monovalent groups obtained by removing one hydrogen atom from bicycloalkanes having 5 to 30 carbon atoms, such as bicyclo[1,2,2]heptan-2-yl, bicyclo[2,2,2]octan-3-yl) and also including tricyclo structures each containing a large number of cyclic structures; alkyl groups in substituents to be illustrated below (e.g., an alkyl group in an alkylthio group) also representing the alkyl groups of the concept given above];

alkenyl groups [representing optionally substituted, linear, branched or cyclic alkenyl groups including alkenyl groups (preferably optionally substituted alkenyl groups having 2 to 30 carbon atoms, such as vinyl, allyl, prenyl, geranyl, and oleyl), cycloalkenyl groups (preferably optionally substituted cycloalkenyl groups having 3 to 30 carbon atoms, i.e., monovalent groups obtained by removing one hydrogen atom from cycloalkenes having 3 to 30 carbon atoms, such as 2-cyclopenten-1-yl, and 2-cyclohexen-1-yl), and bicycloalkenyl groups (optionally substituted bicycloalkenyl groups, preferably optionally substituted bicycloalkenyl groups having 5 to 30 carbon atoms, i.e., monovalent groups obtained by removing one hydrogen atom from bicycloalkenes having a double bond, including, for example, bicyclo[2,2,1]hept-2-en-1-yl, and bicyclo[2,2,2]oct-2-en-4-yl)], alkynyl groups (preferably optionally substituted alkynyl groups having 2 to 30 carbon atoms, such as ethynyl, propargyl and trimethylsilylethynyl groups);

aryl groups (preferably optionally substituted aryl groups having 6 to 30 carbon atoms, such as phenyl, p-tolyl, naphthyl, m-chlorophenyl, and o-hexadecanoylaminophenyl), heterocyclic groups (preferably monovalent groups obtained by removing one hydrogen atom from optionally substituted, 5- or 6-membered, aromatic or non-aromatic heterocyclic compounds, and more preferably 5- or 6-membered heteroaromatic ring groups having 3 to 30 carbon atoms, such as 2-furanyl, 2-thienyl, 2-pyrimidinyl and 2-benzothiazolyl);

cyano group, hydroxyl group, nitro group, carboxyl group, alkoxy groups (preferably optionally substituted alkoxy groups having 1 to 30 carbon atoms, such as methoxy, ethoxy, isopropoxy, t-butoxy, n-octyloxy, and 2-methoxyethoxy), aryloxy groups (preferably optionally substituted aryloxy groups having 6 to 30 carbon atoms, such as phenoxy, 2-methylphenoxy, 4-t-butylphenoxy, 3-nitrophenoxy, and 2-tetradecanoylaminophenoxy), silyloxy groups (preferably silyloxy groups having 3 to 20 carbon atoms, such as trimethylsilyloxy, and t-butyldimethylsilyloxy), heterocyclic oxy groups (preferably optionally substituted heterocyclic oxy groups having 2 to 30 carbon atoms, such as 1-phenyltetrazol-5-oxy, and 2-tetrahydropyranyloxy), acyloxy groups (preferably formyloxy group, optionally substituted alkylcarbonyloxy groups having 2 to 30 carbon atoms, and optionally substituted arylcarbonyloxy groups having 6 to 30 carbon atoms, such as formyloxy, acetyloxy, pivaloyloxy, stearoyloxy, benzoyloxy, and p-methoxyphenylcarbonyloxy), carbamoyloxy groups (preferably optionally substituted carbamoyloxy groups having 1 to 30 carbon atoms, such as N,N-dimethylcarbamoyloxy, N,N-diethylcarbamoyloxy, morpholinocarbonyloxy, N,N-di-n-octylaminocarbonyloxy, and N-n-octylcarbamoyloxy), alkoxycarbonyloxy groups (preferably optionally substituted alkoxycarbonyloxy groups having 2 to 30 carbon atoms, such as methoxycarbonyloxy, ethoxycarbonyloxy, t-butoxycarbonyloxy, and n-octylcarbonyloxy), aryloxycarbonyloxy groups (preferably optionally substituted aryloxycarbonyloxy groups having 7 to 30 carbon atoms, such as phenoxycarbonyloxy, p-methoxyphenoxycarbonyloxy, and p-n-hexadecyloxyphenoxycarbonyloxy);

amino groups (preferably amino group, optionally substituted alkylamino groups having 1 to 30 carbon atoms, and optionally substituted anilino groups having 6 to 30 carbon atoms, such as amino, methylamino, dimethylamino, aniline, N-methyl-anilino and diphenylamino), acylamino groups (preferably formylamino group, optionally substituted alkylcarbonylamino groups having 1 to 30 carbon atoms, and optionally substituted arylcarbonylamino groups having 6 to 30 carbon atoms, such as formylamino, acetylamino, pivaloylamino, lauroylamino, benzoylamino, and 3,4,5-tri-n-octyloxyphenylcarbonylamino), aminocarbonylamino groups (preferably optionally substituted aminocarbonylamino having 1 to 30 carbon atoms, such as carbamoylamino, N,N-dimethylaminocarbonylamino, N,N-diethylaminocarbonylamino, and morpholinocarbonylamino), alkoxycarbonylamino groups (preferably optionally substituted alkoxycarbonylamino groups having 2 to 30 carbon atoms, such as methoxycarbonylamino, ethoxycarbonylamino, t-butoxycarbonylamino, n-octadecyloxycarbonylamino, and N-methyl-methoxycarbonylamino), aryloxycarbonylamino groups (preferably optionally substituted aryloxycarbonylamino groups having 7 to 30 carbon atoms, such as phenoxycarbonylamino, p-chlorophenoxycarbonylamino, and m-n-octyloxyphenoxycarbonylamino), sulfamoylamino groups (preferably optionally substituted sulfamoylamino groups having 0 to 30 carbon atoms, such as sulfamoylamino, N,N-dimethylaminosulfonylamino, and N-n-octylaminosulfonylamino), alkyl- and arylsulfonylamino groups (preferably optionally substituted alkylsulfonylamino having 1 to 30 carbon atoms, and optionally substituted arylsulfonylamino having 6 to 30 carbon atoms, such as methylsulfonylamino, butylsulfonylamino, phenylsulfonylamino, 2,3,5-trichlorophenylsulfonylamino, and p-methylphenylsulfonylamino);

mercapto group, alkylthio groups (preferably optionally substituted alkylthio groups having 1 to 30 carbon atoms, such as methylthio, ethylthio, and n-hexadecylthio), arylthio groups (preferably optionally substituted arylthio having 6 to 30 carbon atoms, such as phenylthio, p-chlorophenylthio, and m-methoxyphenylthio), heterocyclic thio groups (preferably optionally substituted heterocyclic thio groups having 2 to 30 carbon atoms, such as 2-benzothiazolylthio, and 1-phenyltetrazol-5-ylthio), sulfamoyl groups (preferably optionally substituted sulfamoyl groups having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl), sulfo group, alkyl- and arylsulfinyl groups (preferably optionally substituted alkylsulfinyl groups having 1 to 30 carbon atoms, and optionally substituted arylsulfinyl groups having 6 to 30 carbon atoms, such as methylsulfinyl, ethylsulfinyl, phenylsulfinyl and p-methylphenylsulfinyl);

alkyl- and arylsulfonyl groups (preferably optionally substituted alkylsulfonyl groups having 1 to 30 carbon atoms, and optionally substituted arylsulfonyl groups having 6 to 30 carbon atoms, such as methylsulfonyl, ethylsulfonyl, phenylsulfonyl, and p-methylphenylsulfonyl), acyl groups (preferably formyl group, optionally substituted alkylcarbonyl groups having 2 to 30 carbon atoms, optionally substituted arylcarbonyl groups having 7 to 30 carbon atoms, and optionally substituted heterocyclic carbonyl groups having 4 to 30 carbon atoms in which a carbonyl group is bonded to a carbon atom, such as acetyl, pivaloyl, 2-chloroacetyl, stearoyl, benzoyl, p-n-octyloxyphenylcarbonyl, 2-pyridylcarbonyl, and 2-furylcarbonyl), aryloxycarbonyl groups (preferably optionally substituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl), alkoxycarbonyl groups (preferably optionally substituted alkoxycarbonyl groups having 2 to 30 carbon atoms, such as methoxycarbonyl, ethoxycarbonyl, t-butoxycarbonyl, and n-octadecyloxycarbonyl); and carbamoyl groups (preferably optionally substituted carbamoyl having 1 to 30 carbon atoms, such as carbamoyl, N-methylcarbamoyl, N,N-dimethylcarbamoyl, N,N-di-n-octylcarbamoyl, and N-(methylsulfonyl)carbamoyl), aryl- and heterocyclic azo groups (preferably optionally substituted arylazo groups having 6 to 30 carbon atoms, and optionally substituted heterocyclic azo groups having 3 to 30 carbon atoms, such as phenylazo, n-chlorophenylazo, and 5-ethylthio-1,3,4-thiadiazol-2-ylazo), imide groups (preferably N-succinimide, and N-phthalimide), phosphino groups (preferably optionally substituted phosphino groups having 2 to 30 carbon atoms, such as dimethylphosphino, diphenylphosphino, and methylphenoxyphosphino), phosphinyl groups (preferably optionally substituted phosphinyl groups having 2 to 30 carbon atoms, such as phosphinyl, dioctyloxyphosphinyl, and diethoxyphosphinyl), phosphinyloxy groups (preferably optionally substituted phosphinyloxy groups having 2 to 30 carbon atoms, such as diphenoxyphosphinyloxy, and dioctyloxyphosphinyloxy), phosphinylamino groups (preferably optionally substituted phosphinylamino groups having 2 to 30 carbon atoms, such as dimethoxyphosphinylamino, and dimethylaminophosphinylamino), silyl groups (preferably optionally substituted silyl groups having 3 to 30 carbon atoms, such as trimethylsilyl, t-butyldimethylsilyl, and phenyldimethylsilyl).

Of the foregoing functional groups, ones having a hydrogen atom may be further substituted with any of the foregoing groups after removal of the hydrogen atom. Examples of such functional groups include alkylcarbonylaminosulfonyl groups, arylcarbonylaminosulfonyl groups, alkylsulfonylaminocarbonyl groups, and arylsulfonylaminocarbonyl groups. Exemplary groups include methylsulfonylaminocarbonyl, p-methylphenylsulfonylaminocarbonyl, acetylaminosulfonyl, and benzoylaminosulfonyl groups.

The structure represented by $(CR_3R_4)_m$ is preferably —$CH_2$—, —$CH_2CH_2$—, —$CH_2CH(CH_3)$—, —$CH_2CH_2CH_2$—, —$CH_2CH(OH)CH_2$—, or —$CH_2CH(CH_2OH)$—, more preferably —$CH_2$—, —$CH_2CH_2$—, —$CH_2CH(OH)CH_2$—, or —$CH_2CH_2CH_2$—, and most preferably —$CH_2$— or —$CH_2CH_2$—.

l represents an integer of 1 to 6. In particular, l is preferably 1 to 5 and more preferably 2 to 4 in terms of more excellent affinity for a fluorine-containing polymer and a fluorine-containing solvent.

q represents 0 or 1, p represents 2 or 3, and p+q represents 3. In particular, q is preferably 1 and p is preferably 2 in terms of more excellent affinity for a fluorine-containing polymer and a fluorine-containing solvent.

X represents a perfluoroalkyl group having 1 to 14 carbon atoms. The perfluoroalkyl group may be linear or branched.

Examples of the linear or branched perfluoroalkyl group having 1 to 14 carbon atoms include $CF_3$—, $C_2F_5$—, $C_3F_7$—, $C_4F_9$—, $C_5F_{11}$—, $C_6F_{13}$—, $C_7F_{15}$—, $C_8F_{17}$—, $C_9F_{19}$—, $C_{10}F_{21}$—, $C_{12}F_{25}$—, and $C_{14}F_{29}$—.

Examples of the preferable structure of the perfluoroalkyl group represented by —$(CF_2)_l$—$C((F)_q((X)_p)$ include $(CF_3)_2$—CF—$(CF_2)_2$—, $(CF_3)_2$—CF—$(CF_2)_4$—, $CF_3(CF_2)_3$—CF($CF_2CF_3$) $CF_2$—, $(CF_3)_2$—CF—$(CF_2)_6$—, $(CF_3)_3$—C—$(CF_2)_2$—, $(CF_3)_2$—CF—$CF_2$—, and $(CF_3(CF_2)_3)(CF_3CF_2)$ CF—$CF_2$—.

Examples of the compound represented by formula (1) according to the invention are illustrated below but the present invention is not limited thereto.

[Chemical Formula 2]

1-1
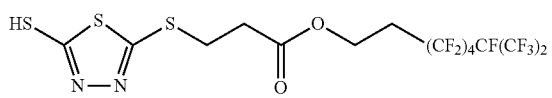

1-2
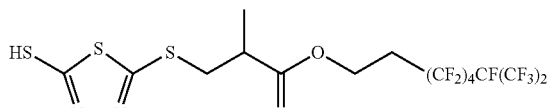

1-3
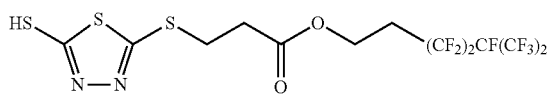

1-4
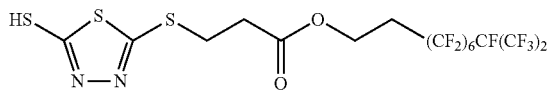

1-5
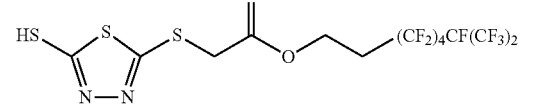

1-6
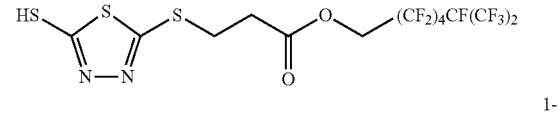

1-7
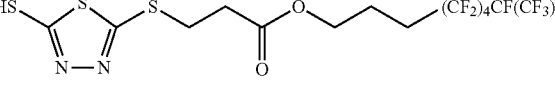

1-8

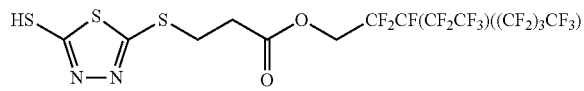

(Method of Producing Compound Represented by Formula (1))

The method of producing the compound represented by formula (1) is not particularly limited and the compound represented by formula (1) can be produced by combining known methods.

For example, the compound represented by formula (1) can be produced by a step shown in Scheme 1 or Scheme 2 shown below but the production method is not limited thereto.

(Scheme 1)

[Chemical Formula 3]

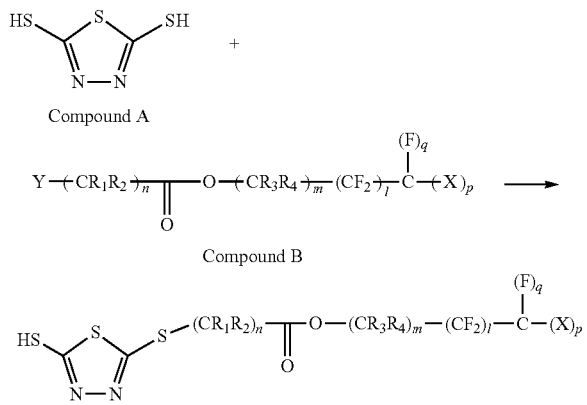

As shown in Scheme 1, Compound A (1,3,4-thiadiazole-2,5-dithiol) and Compound B having a leaving group Y are prepared and both the compounds are reacted, whereby a desired compound represented by formula (1) can be synthesized.

The type of the leaving group Y in Compound 3 is not particularly limited and preferable examples thereof include chlorine atom, bromine atom, iodine atom, fluorine atom, methanesulfonyloxy group, benzenesulfonyloxy group, p-toluenesulfonyloxy group, trifluoromethanesulfonyloxy group and nonafluorobutanesulfonyloxy group.

The foregoing reaction may be carried out in the presence of a base if necessary. Any known compound can be used as the base for use in the reaction and the base is preferably selected from among, for example, organic bases (e.g., triethylamine, trimethylamine, diisopropylethylamine, pyridine, morpholine, 1,4-diazabicyclo[2.2.2]octane, 1,5-diazabicyclo[4.3.0]non-5-ene, 1,8-diazabicyclo[5.4.0]undec-7-ene, sodium methoxide, potassium methoxide, sodium ethoxide, potassium ethoxide, butyllithium, t-butyllithium, and sec-butyllithium), inorganic bases (e.g., sodium carbonate, potassium carbonate, sodium hydrogen carbonate, potassium hydrogen carbonate, sodium hydroxide, potassium hydroxide, lithium hydroxide, cesium hydroxide, calcium hydroxide, potassium hydride, sodium hydride, and lithium aluminum hydride).

It should be noted that the foregoing reaction may be carried out in the presence of a solvent if necessary. The type of the solvent to be used is not particularly limited and examples thereof include water and organic solvents.

Next, unreacted materials, by-products and other impurities are separated for refinement if necessary to obtain the compound represented by formula (1). Separation and refinement need only be performed by a common method, and examples thereof include an extraction operation using an organic solvent, recrystallization, crystallization using a poor solvent, and column chromatography using silica gel.

$R_1$, $R_2$, $R_3$ and $R_4$ as well as n, m, l, p and q of Compound B in Scheme 1 are as defined above.

(Scheme 2)

[Chemical Formula 4]

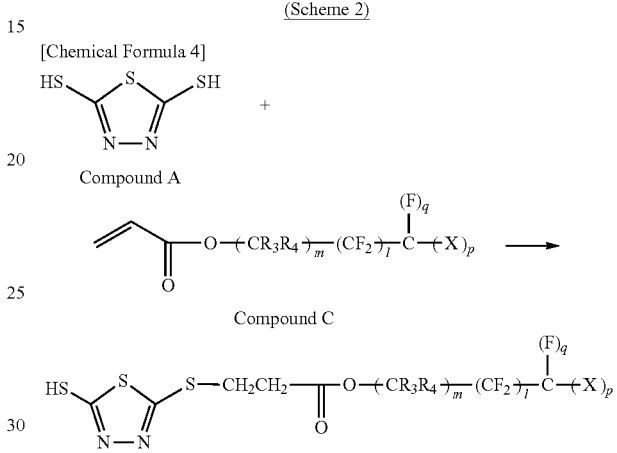

As shown in Scheme 2, Compound A (1,3,4-thiadiazole-2,5-dithiol) and Compound C having an acryloyl group (acrylic acid ester) are prepared and both the compounds are reacted, whereby a desired compound corresponding to the compound represented by formula (1) can be synthesized.

It should be noted that the foregoing reaction may be carried out in the presence of a solvent if necessary. The type of the solvent to be used is not particularly limited and examples thereof include water and organic solvents.

The foregoing reaction may be carried out in the presence of a base described for Scheme 1 if necessary.

Various types of separation and refinement described for Scheme 1 may be carried out after the end of the reaction if necessary.

$R_3$ and $R_4$ as well as m, l, p and q of Compound C in Scheme 2 are as defined above.

The compound represented by formula (1) can be used in various applications.

In addition, the compound represented by formula (1) has excellent affinity for a fluorine-containing polymer (fluororesin) and a fluorine-containing solvent. Examples of the fluorine-containing polymer include known fluorine atom-containing polymers (e.g., polytetrafluoroethylene, polyvinylidene fluoride, polyvinyl fluoride, and a cyclized polymer of perfluoro(butenylvinylether) (Cytop (registered trademark))). The fluorine-containing polymer may also be a polymer obtained by polymerizing a fluorine-containing ethylenic monomer. Examples of the fluorine-containing ethylenic monomer include vinylidene fluoride, tetrafluoroethylene, hexafluoropropylene, vinyl trifluorochloride, vinyl fluoride, perfluoroalkyl vinyl ether, fluorine-containing (meth)acrylic monomers (e.g., 1H,1H,2H,2H-heptadecafluorodecyl methacrylate, 1H,1H,5H-octafluoropentyl methacrylate, 2,2,3,3-tetrafluoropropyl methacrylate, 2,2,2-trifluoroethyl methacrylate, 1H,1H,2H,2H-heptadecafluorodecyl acrylate, 1H,1H,5H-octafluoropentyl acrylate, 2,2,3,3-tetrafluoropropyl acrylate, 2,2,2-trifluoroethyl acrylate, perfluorooctylethyl methacrylate, and perfluorooctylethyl acrylate).

An example of the fluorine-containing solvent includes a known fluorine atom-containing solvent. Examples of the fluorine-containing solvent include a fluorine-modified aliphatic hydrocarbon solvent, a fluorine-modified aromatic hydrocarbon solvent, a fluorine-modified ether solvent, and a fluorine-modified alkylamine solvent. Specific examples of the fluorine-containing solvent that may be illustrated include polyfluorotrialkylamine compounds (fluorine-modified alkylamine solvents) such as perfluorobenzene, pentafluorobenzene, 1,3-bis(trifluoromethyl)benzene, 1,4-bis(trifluoromethyl)benzene, perfluorotributylamine, perfluorotripropylamine and perfluorotripentylamine; fluorine-modified aliphatic hydrocarbon solvents such as perfluorodecalin, perfluorocyclohexane, perfluoro(1,3,5-trimethylcyclohexane), perfluoro(2-butyltetrahydrofuran), perfluorohexane, perfluorooctane, perfluorodecane, perfluorododecane, perfluoro(2,7-dimethyloctane), 1,1,2-trichloro-1,2,2-trifluoroethane, 1,1,1-trichloro-2,2,2-trifluoroethane, 1,3-dichloro-1,1,2,2,3-pentafluoropropane, 1,1,1,3-tetrachloro-2,2,3,3-tetrafluoropropane, 1,1,3,4-tetrachloro-1,2,2,3,4,4-hexafluorobutane, perfluoro(1,2-dimethylhexane), perfluoro(1,3-dimethylhexane), 2H,3H-perfluoropentane, 1H-perfluorohexane, 1H-perfluorooctane, 1H-perfluorodecane, 1H,1H,1H,2H,2H-perfluorohexane, 1H,1H,1H,2H,2H-perfluorooctane, 1H,1H,1H,2H,2H-perfluorodecane, 3H,4H-perfluoro-2-methylpentane, 2H,3H-perfluoro-2-methylpentane, 1H-1,1-dichloroperfluoropropane, 1H-1,3-dichloroperfluoropropane, and perfluoroheptane; fluorine-modified aromatic hydrocarbon solvents such as m-xylene trifluoride, m-xylene hexafluoride and benzotrifluoride; and fluorine-modified ether solvents such as methyl perfluorobutyl ether, and perfluoro(2-butyltetrahydrofuran).

EXAMPLES

The present invention is described below in further detail by way of examples. However, the invention should not be construed as being limited to the following examples. Unless otherwise specified, the ratio is expressed by percentage by weight.

Example 1

Synthesis of Compound 1-1

Compound 1-1 was synthesized according to the following scheme.

[Chemical Formula 5]

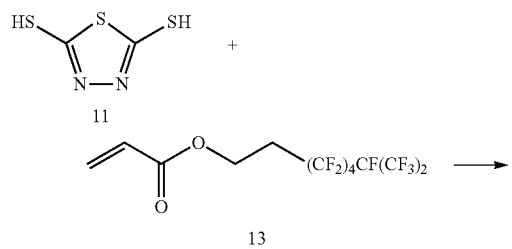

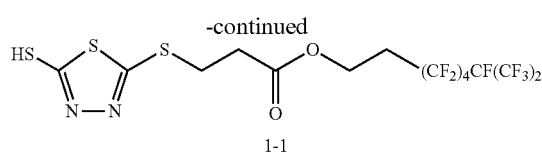

1-1

1,3,4-Thiadiazole-2,5-dithiol (Wako Pure Chemical Industries, Ltd.) (4.0 g, 26.6 mmol) and tetrahydrofuran (80 mL) were added to a reaction vessel and completely dissolved. Thereafter, 3,3,4,4,3,5,6,6,7,8,8,8,-dodecafluoro-7-(trifluoromethyl)octyl acrylate (12.5 g, 26.6 mmol) was added dropwise to the reaction solution from a dropping funnel over 0.5 hour. The reaction solution was stirred at 65° C. for 6 hours and then cooled to room temperature and concentrated under reduced pressure. Hexane (200 mL) was added to the reaction solution and the solution was cooled in an ice bath to obtain 16 g of crude crystals. A portion of the crude crystals (8 g) were purified by silica gel column chromatography (mobile phase: hexane/ethyl acetate=2/1 to 1/1) to obtain 6 g of Compound 1-1 of the invention (yield: 72%).

The resulting Compound 1-1 according to the invention has the following $^1$H-NMR spectrum:

$^1$H-NMR (solvent: deuterated chloroform; reference: tetramethylsilane)

11.1 (1H, br), 4.44 (2H, t), 3.40 (2H, t), 2.85 (2H, t), 2.49 (2H, t), 2.49 (2H, m)

The resulting compound was identified as Compound 1-1 of the invention since each proton peak was observed at a characteristic position in the $^1$H-NMR data.

Compounds 1-2 to 1-8 illustrated above as specific examples of the compound represented by formula (1) were synthesized in the same manner using the synthesis method of Example 1 and a method which is already known in a literature.

<Solubility Check>

(Testing Method)

To a mixed solution of perfluorotributylamine/1,1,1,3,3,3-hexafluoropropan-2-ol/Cytop CTL-809M (manufactured by Asahi Glass Co., Ltd.)=90/5/5 (parts by weight), was added the compound represented by formula (1) according to the invention (any of Compounds 1-1 to 1-8) or any of Comparative Compounds C-1 to C-3 as shown below in an amount of 0.3 wt % with respect to the Cytop CTL-809M. Thereafter, the mixed solution was applied onto a glass substrate to a film thickness of 2 μm and dried.

The surface profile of the resulting coated film was observed by an optical microscope to check whether each compound bled out or remained partially undissolved.

Compounds which neither bleed out nor remain partially undissolved are denoted by "Compatible," compounds which bleed out are denoted by "Bleed out," and a compound which remains partially undissolved is denoted by "Remain partially undissolved."

[Chemical Formula 6]

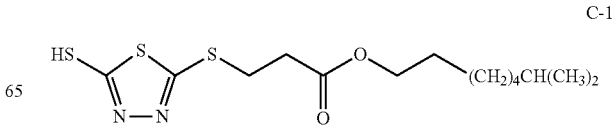

C-1

-continued

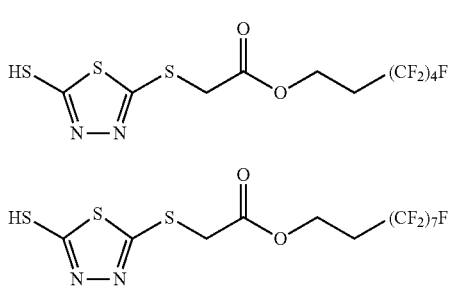

TABLE 1

| Compound | Solubility | Remark |
| --- | --- | --- |
| Compound 1-1 | Compatible | Present Invention |
| Compound 1-2 | Compatible | Present Invention |
| Compound 1-3 | Compatible | Present Invention |
| Compound 1-4 | Compatible | Present Invention |
| Compound 1-5 | Compatible | Present Invention |
| Compound 1-6 | Compatible | Present Invention |
| Compound 1-7 | Compatible | Present Invention |
| Compound 1-8 | Compatible | Present Invention |
| Compound C-1 | Remain partially undissolved | Comparative Example |
| Compound C-2 | Bleed out | Comparative Example |
| Compound C-3 | Bleed out slightly | Comparative Example |

When Comparative Compound C-1 free from a fluorine-containing alkyl group was used, the compound remained partially undissolved. When Comparative Compounds C-2 and C-3 which included a fluorine-containing alkyl group but fell outside the scope of this application were used, the compounds bled out on the resin surface.

In contrast, the compounds of formula (1) according to the invention are found to exhibit excellent compatibility with resin and to have high affinity for fluorine materials. From the above, the beneficial effects of the invention are obvious.

What is claimed is:

1. A compound represented by formula (1) shown below:

[Chemical Formula 1]

Formula (1)

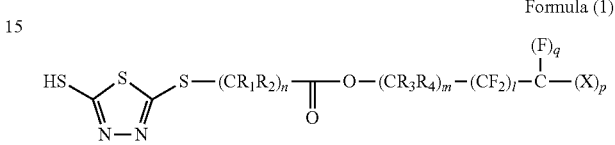

(in formula (1), $R_1$ and $R_2$ each independently represent a hydrogen atom or an alkyl group; $R_3$ and $R_4$ each independently represent a hydrogen atom or a substituent; n represents 1 or 2; m represents an integer of 1 to 6; l represents an integer of 1 to 6; q represents 0 or 1; p represents 2 or 3; p+q represents 3; X represents a perfluoroalkyl group having 1 to 14 carbon atoms; when n is 2, structures of units represented by $CR_1R_2$ may be identical to or different from each other; and when m is 2 or more, structures of units represented by $CR_3R_4$ may be identical to or different from each other).

* * * * *